(12) United States Patent
Hara et al.

(10) Patent No.: US 8,564,779 B2
(45) Date of Patent: Oct. 22, 2013

(54) ADSORPTIVE GAS ANALYZER

(75) Inventors: Kenji Hara, Kyoto (JP); Montajir Rahman, Kyoto (JP); Shigeru Nakatani, Kyoto (JP); Masahiro Nakane, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 13/109,876

(22) Filed: May 17, 2011

(65) Prior Publication Data

US 2011/0285998 A1 Nov. 24, 2011

(30) Foreign Application Priority Data

May 18, 2010 (JP) .................................. 2010-114813
Mar. 9, 2011 (JP) .................................. 2011-052090

(51) Int. Cl.
*G01N 21/00* (2006.01)

(52) U.S. Cl.
USPC .......................................... 356/437; 356/432

(58) Field of Classification Search
USPC .......... 356/432–444; 250/338.5, 343, 339.13, 250/339.12, 339.06; 73/335.01, 29.05, 23.2
See application file for complete search history.

(56) References Cited

U.S. PATENT DOCUMENTS

| 7,354,553 B2* | 4/2008 | Appel et al. .................. 422/91 |
| 2006/0044562 A1 | 3/2006 | Hagene et al. |
| 2007/0273882 A1* | 11/2007 | Smith ......................... 356/437 |
| 2008/0092648 A1 | 4/2008 | Zhou et al. |

FOREIGN PATENT DOCUMENTS

| JP | 1997061361 | 3/1997 |
| JP | 2001-159587 | 6/2001 |

* cited by examiner

*Primary Examiner* — Tri T Ton
(74) *Attorney, Agent, or Firm* — Brooks Kushman P.C.

(57) ABSTRACT

This invention makes it possible to measure a concentration of a gas component having the adsorption even thought the concentration is low, and to improve a response speed of the measurement of the concentration, and comprises a body that has an introduction port to introduce a sample gas into a measurement cell, a laser light irradiation part that irradiates the laser light on the measurement cell, a heating pipe that applies heat to the sample gas introduced into the introduction port, a flow rate limit part that makes the sample gas at a negative pressure and that introduces the negative-pressurized heated sample gas into the body, and a negative pressure pump that keeps inside of the measurement cell and a flow channel from a downstream side of the flow rate limit part to the measurement cell at the negative pressure.

2 Claims, 3 Drawing Sheets

ADSORPTIVE GAS ANALYZER

CROSS-REFERENCE TO RELATED APPLICATIONS

This application claims priority to Japanese Patent Application No. 2010-114813 filed May 18, 2010 and Japanese Patent Application No. 2011-052090 filed Mar. 9, 2011, the disclosures of which are incorporated in their entirety by reference herein.

FIELD OF THE ART

This invention relates to a gas analyzer that measures a concentration of a component of a gas having the adsorption such as an ammonia ($NH_3$) component or a hydrocarbon (HC) component contained in a sample gas such as an exhaust gas.

BACKGROUND ART

Recently, due to growing interest in an environmental problem, it has been demanded further more reduction of an amount of NOx emission from an automobile. Then, various kinds of NOx after treatment devices such as a lean NOx trap catalyst for gasoline engine or a selective catalytic reduction (SCR) for diesel engine have been actively researched and developed. In order to evaluate NOx after treatment devices, a measurement of various nitrogen compounds such as NO, NO2, N2O, NH3 gets attention. Especially, for evaluation of the selective catalytic reduction (SCR), the measurement of NH3 becomes important to evaluate NH3 slip. In addition, since there is a regulation on NH3 in the EURO VI scheduled to be enforced in 2014 in EU, a measurement that can be conducted at a low concentration of NH3 with high response speed is required.

As shown in the patent document 1, a conventional gas analyzer used for measuring a concentration of NH3 introduces an exhaust gas emitted from an exhaust pipe of an automobile into a measurement cell by means of a sampling pipe and measures the concentration of NH3 by the use of a light absorbance of NH3.

However, with the gas analyzer of this sampling method, there is a problem that NH3 contained in the exhaust gas is highly adherent and attaches to an inner wall of the sampling pipe or an inner wall of a flow rate control device arranged on a pipe. As a result, there is a problem that it is difficult to measure the concentration of NH3 with high accuracy. Especially, the concentration of the NH3 contained in the exhaust gas is low so that it takes time to introduce the exhaust gas into the measurement cell due to the inner wall of the pipe. As a result of this, the response speed is lowered so that there is a problem that it is difficult to conduct the measurement at a high speed.

In addition, with the gas analyzer of this sampling method, a suction pump is arranged between the sampling pipe and the measurement cell to sample the exhaust gas and to introduce the sampled sample gas into the measurement cell.

However, in case that the exhaust gas is sampled by the use of the suction pump, a pressure of inside of the sampling pipe fluctuates between a negative pressure and a positive pressure by the pressure of the exhaust gas emitted from the exhaust pipe (a tail pipe). In case that the pressure becomes at the positive pressure, NH3 easily attaches to the inner wall of the sampling pipe. In addition, the measurement of the concentration conducted in the measurement cell is a Fourier transform infrared spectroscopy (FTIR) or a Non-dispersive infrared analyzing method (NDIR). In order to conduct the measurement, it is required that the pressure in the measurement cell is made generally the same as the atmospheric pressure. With this arrangement, there is a problem that NH3 attaches to inside of the measurement cell. Furthermore, with this arrangement, since the exhaust gas introduced into the measurement cell passes a pump, there is also a problem that $NH_3$ attaches to the pump.

PRIOR ART DOCUMENT

Patent Document

Patent document 1: Japan patent laid-open number 2001-159587

DISCLOSURE OF THE INVENTION

Problems to be Solved by the Invention

In order to solve all of the problems the present claimed invention focuses attention on that there is no need of measuring the sample gas in the measurement cell at generally the same pressure as the atmospheric pressure if the gas component is analyzed by the absorptiometry by the use of the laser light and a main object of this invention is to make it possible to measure the concentration of the adsorptive gas component having a polar characteristic such as $NH_3$ component or HC component with high accuracy even though the concentration is low and to improve the response speed of the concentration measurement.

Means to Solve the Problems

More specifically, the adsorptive gas analyzer in accordance with this invention is to measure a concentration of an adsorptive component having a polar character contained in a sample gas, and is characterized by comprising a body that has a measurement cell to measure the sample gas and an introduction port to introduce the sample gas into the measurement cell, a laser light irradiation part that irradiates the laser light on the measurement cell, a heating pipe that is connected to the introduction port and that applies heat to the sample gas introduced into the introduction port, a flow rate limit part that makes the sample gas at a negative pressure and that introduces the negative-pressurized heated sample gas into the body, and a negative pressure pump that is connected to the measurement cell, that keeps inside of the measurement cell at the negative pressure from a starting time of a sampling to an ending time of the measurement and that keeps a flow channel from a downstream side of the flow rate limit part to the measurement cell at the negative pressure from the starting time of the sampling to the ending time of the measurement.

In accordance with this arrangement, since the heating pipe and the flow rate limit part are arranged outside of the body and inside of the measurement cell and the flow channel from the downstream side of the flow rate limit part to the measurement cell are made at the negative pressure by means of the negative pressure pump, it is possible to enlarge the area at the negative pressure in the flow channel connected to the measurement cell, thereby enabling to reduce adsorption of the adsorptive gas component having the polar character such as $NH_3$ or HC. In addition, since the flow rate limit part is arranged and the negative pressure is kept by the negative pressure pump from the starting time of the sampling to the ending time of the measurement, it is possible to prevent the downstream side of the flow rate limit part from being at a positive pressure due to a flowing pressure of the sample gas, thereby enabling to prevent attachment of the adsorptive gas component. With this arrangement, it is possible to measure the concentration of the adsorptive gas having a polar character such as the $NH_3$ component or the HC component with high accuracy even though its concentration is low, and furthermore it is possible to improve the response speed of measuring the concentration. In addition, since the negative pressurized sample gas is heated by the heating pipe, it is possible to prevent a dissolution loss of the adsorptive gas component associated with the due condensation in the pipe, thereby enabling to further improve the measurement accuracy and the response speed. Furthermore, if the absorption spectrum at an atmospheric pressure is monitored, it is known that the absorption peak is wide. Then if inside of the measurement cell is kept at the negative pressure, it is possible to obtain a sharper peak, thereby enabling to reduce an interference influence on the absorption peak by the adsorptive gas component.

If the inside of the measurement cell and the flow channel of the heating pipe from the downstream side of the flow rate limit part to the measurement cell is kept at the negative pressure, it is possible to reduce the adsorption amount of the adsorptive gas component attaching to the inner wall. However, with this arrangement, the amount of the sample gas introduced into the measurement cell is also decreased. As a result, there is a problem that the obtained detected signal is decreased so that the detecting sensitivity is deteriorated. In order to solve this problem, it is preferable that the measurement cell is of a multiple reflection type. With this arrangement, it is possible to lengthen the optical length in the measurement cell so that the detected signal is increased, thereby enabling to improve the detecting sensitivity. Especially, it is effective for measuring the concentration of the gas of low concentration such as $NH_3$ contained in the sample gas. Since this invention irradiates the laser light, it is possible to elongate the optical length effectively if the cell of the multiple reflection type is used.

Effect of the Invention

In accordance with this invention having the above-mentioned arrangement, it is possible to measure a concentration of an adsorptive gas component having a polar character such as $NH_3$ even though the concentration is low, and to improve a response speed of the measurement of the concentration.

BEST MODES OF EMBODYING THE INVENTION

One embodiment of an exhaust gas analyzer 100 in accordance with this invention will be explained with reference to drawings.

The exhaust gas analyzer 100 in accordance with this embodiment is connected to, for example, an exhaust pipe (a tail pipe) of an automobile, and measures a concentration of NO, $NO_2$, $N_2O$ and $NH_3$ contained in an exhaust gas as being a sample gas emitted from the exhaust pipe by the use of an absorptiometry.

Figure 1:
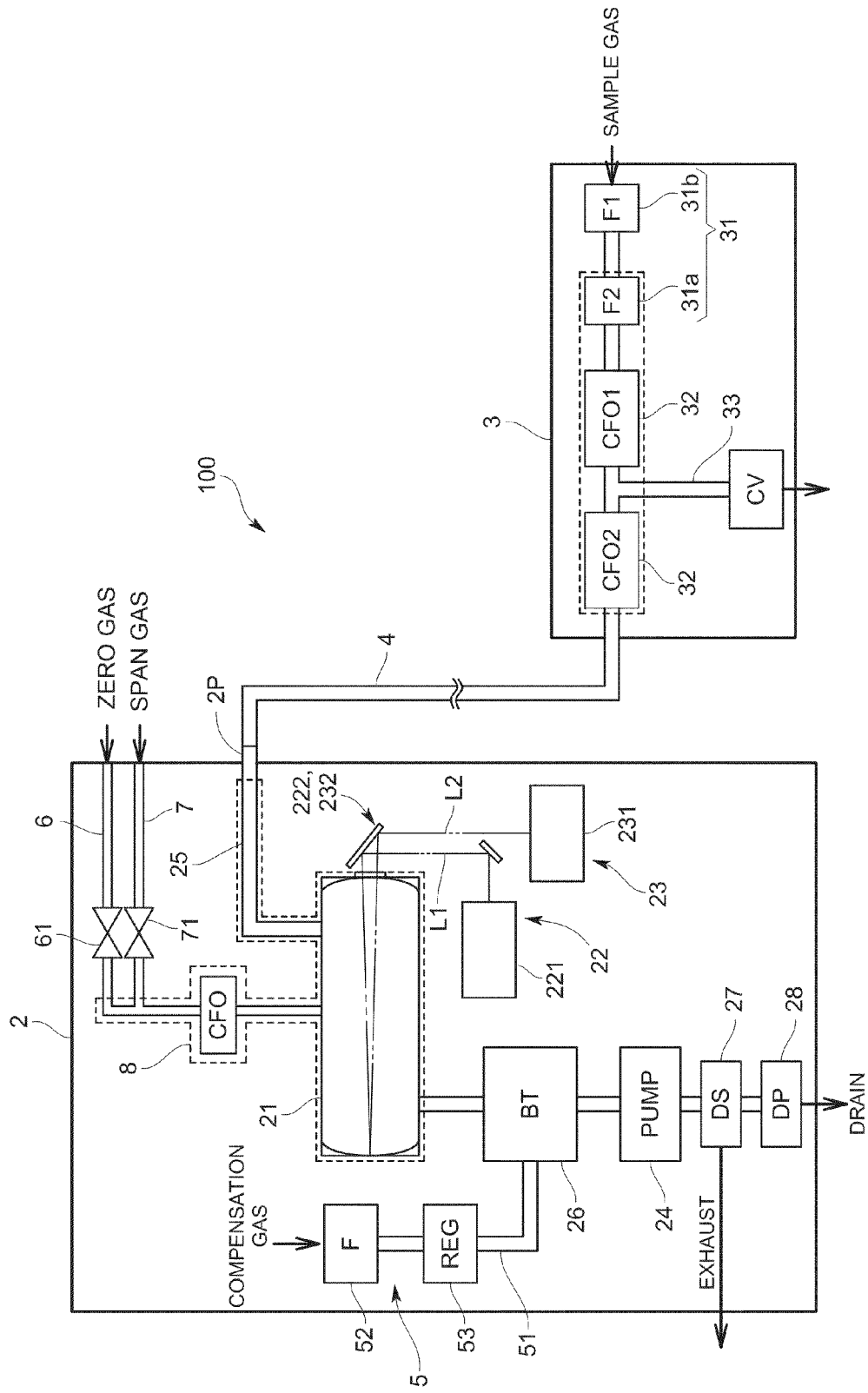
FIG. 1 is a configuration diagram schematically showing an exhaust gas analyzer in accordance with this embodiment.

Concretely, the exhaust gas analyzer 100 comprises, as shown in FIG. 1, a body 2 to measure the sample gas, a flow rate control unit 3 that is arranged separately from the body 2 and that is mounted on the exhaust pipe of the automobile, and a heating pipe 4 that is connected to the body 2 and the flow rate control unit 3 and that introduces the exhaust gas introduced from the flow rate control unit 3 into the body 2. The body 2 and the flow rate control unit 3 are arranged at a different position respectively, and connected by only the heating pipe 4 without any additional casing that houses both the body 2 and the flow rate control unit 3.

Figure 2:
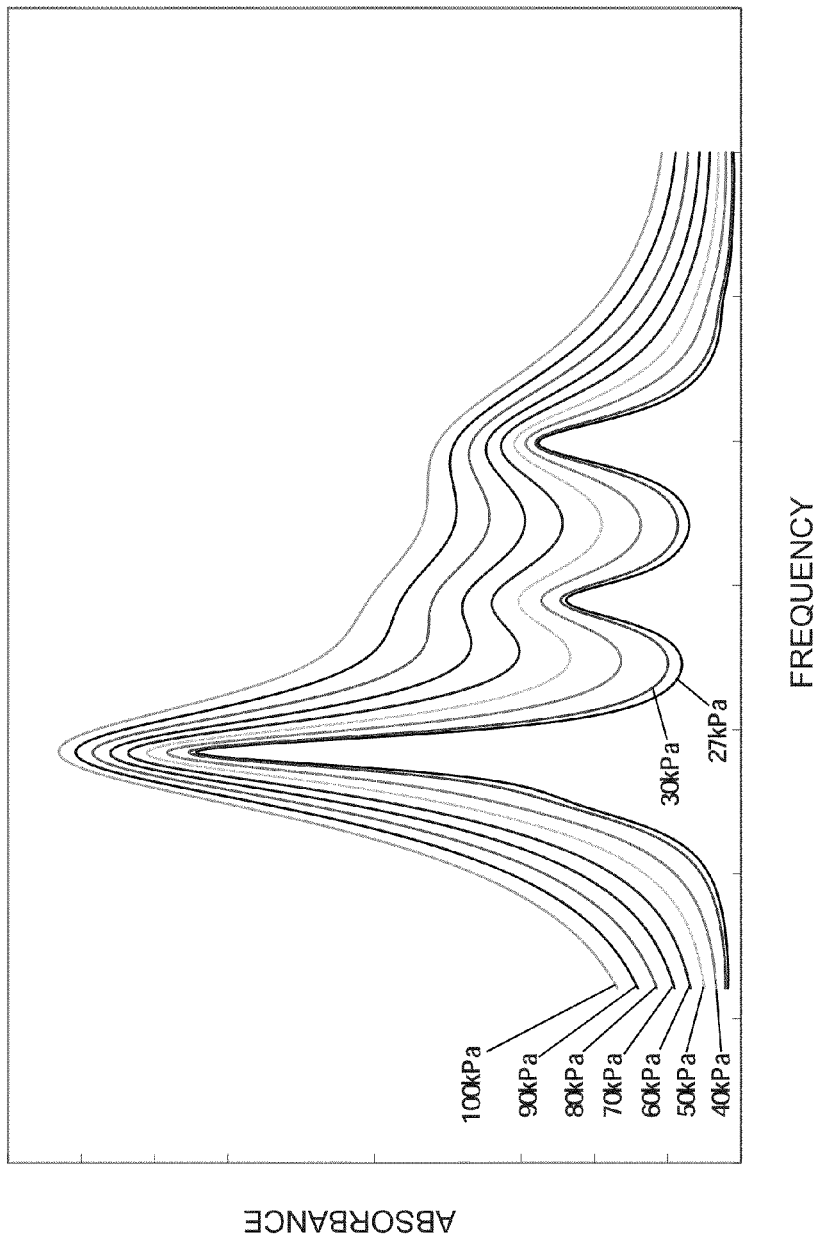
FIG. 2 is a view showing a pressure fluctuation of an absorption spectrum of a sample gas having the adsorption.

The body 2 comprises a measurement cell 21 of a multiple reflection type that measures the sample gas, a laser light irradiation part 22 that irradiates the laser light L1 having high linearity on the sample gas in the measurement cell 21 by introducing the laser light L1 from a light introducing window of the measurement cell 21, a light detecting part 23 that detects the transmitted laser light L2 coming from the measurement cell 21, and a negative pressure pump 24 that is connected to the measurement cell 21 and that makes inside of the measurement cell 21 at a negative pressure. Since the measurement cell 21 is of the multiple reflection type, it is possible to heighten the detection sensitivity even though the concentration of the measurement component is low. In addition, the negative pressure pump 24 keeps the inside of the measurement cell 21 at the negative pressure within a range, for example, between 1 kPa (at this pressure it becomes difficult to conduct the measurement because the gas concentration is too small) and 80 kPa (at this pressure interference with other gas component occurs easily because the peak is broad), and preferably keeps the inside of the measurement cell 21 at the negative pressure within a range between 20 kPa and 50 kPa that is a pressure range at which adsorption of $NH_3$ is difficult to occur, and the interference with other gas component does not occur with realizing a gas concentration that can be measured. As mentioned, if the negative pressure falls within 20 kPa through 50 kPa, it is possible to make both a pressure in the measurement cell 21 and a pressure in the heating pipe 4 equal by means of the single negative pressure pump 24. As shown in FIG. 2, for the absorption spectrum of the sample gas having the adsorptive gas component, a peak begins to form at less than or equal to 80 kPa and its peak is clearly expressed at less than or equal to 50 kPa.

Furthermore, the body 2 has an introduction port 2P to which the heating pipe 4, to be described later, is connected and that is to introduce the exhaust gas flowing in the heating pipe 4 into the measurement cell 21. In order to prevent dew condensation of moisture in the exhaust gas, the introduction port 2P, the internal connecting pipe 25 and the measurement cell 21 are heated at, for example, 113° C. or 191° C.

The laser light irradiation part 22 comprises a laser light source 221 to irradiate the laser light L1, and a guide mechanism 222 comprising a reflection mirror to guide the light from the laser light source 221 to the measurement cell 21. In this embodiment, an object as the adsorptive gas component is $NH_3$, and it can be conceived that the laser light source 221 uses a tunable laser that irradiates the laser light having an infrared region wavelength such as a mid-infrared region or a near-infrared region where $NH_3$ has an absorption property or the laser light having an oscillation wavelength in an ultraviolet region, and uses, for example, a quantum cascade laser (QCL), a semiconductor laser such as a tunable semiconductor laser, a solid laser or a liquid laser.

It is especially preferable to use the quantum cascade laser (QCL) as the laser light source 221. A quantum cascade laser element oscillates the laser light by means of an electric current pulse having a certain interval. Since an oscillation frequency from the laser element depends on the temperature, the oscillation frequency repeats a scan in a narrow frequency range in terms of result. The absorptionmetric method using the QCL (QCL-IR method) uses an element whose oscillation central frequency is adjusted so as to fall the absorption peak position of a component as a target within this frequency range. As will be described later, since a density of the adsorptive gas component such as $NH_3$ in the sample gas is small and its absorption peak becomes small in the negative-pressurized measurement cell 21, the sensitivity drops. However, if the QCL having an oscillation wavelength (a pulse width is 500 nsec) in the near-infrared region is used, it is possible to make the absorption peak big. As a result, it is possible to measure the concentration of the adsorptive gas component without deteriorating the sensitivity under the negative pressure and to obtain a high speed response.

The light detecting part 23 detects the transmitted laser light L2 from the measurement cell 21 after multiple reflection in the measurement cell 21, and it can be conceived to use, for example, an MCT (HgCdTe) detector 23 of a normal temperature operation type. A guide mechanism 232 comprising a reflection mirror to guide the transmitted laser light L2 to the light detector 231 is arranged between the MCT detector 231 and the measurement cell 21. The light intensity signal obtained by the light detector 231 is output to a calculation device, not shown in drawings. The light absorption of each component is calculated and then the concentration of each component is calculated by the calculation device.

The flow rate control unit 3 is connected to the exhaust pipe of the automobile, and comprises a filter 31 to remove a dust in the exhaust gas emitted from the exhaust pipe and a flow rate limit part 32 to limit a flow rate of the exhaust gas passing the filter 31. In addition, it is preferable that the flow rate control unit 3 is mounted directly on an exhaust opening or on a position within 2 m from the exhaust opening through a piping. It is especially preferable that the flow rate control unit 3 is mounted on a position within 50 cm from the exhaust opening. With this arrangement, it is possible to make the exhaust gas from the exhaust pipe at the negative pressure in the upstream side at an early stage.

The filter 31 comprises, for example, a cylindrical filter 31a that is arranged in the upstream side and that can be exchanged by a user, and, for example, a disk-shaped filter 31b that is arranged inside of the flow rate control unit 3 and in the downstream side and that can not be exchanged by a user. In addition, a critical flow orifice (CFO) is used as the flow rate limit part 32 to shorten a response time by lessening an area to contact the gas. Since the flow rate control unit 3 is a unit having the filter 31 and the critical flow orifice (CFO), it can be downsized.

Concretely, the flow rate limit part 32 comprises two critical flow orifices CFO1 and CFO2 arranged in serial. In addition, a bifurcated flow channel 33 having a check valve CV is arranged between two critical flow orifices CFO1 and CFO2. With this arrangement, in case that the exhaust gas flowing in the flow rate control unit 3 is at a high pressure, a part of the sample gas is discharged outside from the bifurcated flow channel 33. In addition, the heating pipe 4, to be described later, is connected to the critical flow orifice CFO2 in the downstream side. In order to prevent dew condensation of moisture in the exhaust gas, the filter 31 and the flow rate limit part 32 are heated at, for example, 113° C. or 191° C.

The heating pipe 4 connects the body 2 and the flow rate control unit 3, each of which is separately arranged, and comprises a pipe surrounded by a heater. Concretely, a downstream side of the heating pipe 4 is connected to the introduction port 2P of the body 2 and an upstream side of the heating pipe 4 is connected to the flow rate limit part 32 (concretely, the critical flow orifice CFO2) of the flow rate control unit 3.

The heating pipe 4 applies heat to the exhaust gas passing the flow rate control unit 3 at 100° C. through 200° C. and introduces the heated exhaust gas into the introduction port 2P of the body 2. If a temperature of the exhaust gas is lower than 100° C., the adsorptive gas component such as $NH_3$ gas is easily adsorbed or condensed in the heating pipe 4. Meanwhile, if the temperature of the exhaust gas is higher than 200° C., in case that the heating pipe 4 is made of, for example, a fluorocarbon resin (PTFE), the PTFE might melt. In this embodiment, the exhaust gas is heated at 113° C. that is the same temperature as the heated temperature of the measurement cell 21 and introduced into the introduction port 2P of the body 2. With this arrangement, the flow rate limit part 32 is arranged in the upstream side end part of the heating pipe 4.

As a material of a pipe of the heating pipe 4 conceived is a stainless steel (SUS) or a fluorocarbon resin (PTEE), however, it is preferable to use the fluorocarbon resin (PTEE) in order to reduce adsorption of $NH_3$ and to shorten a response time. In case that the stainless steel (SUS) is used, it can be conceived that an inner surface of the heating pipe 4 is coated with a porous material such as porous silicon so as not to adsorb the $NH_3$ gas as being a polar molecule. In addition, it is possible to further decrease adsorption of $NH_3$ by providing a surface treatment or a mirror finishing on an inner wall surface of the heating pipe 4.

Figure 3:
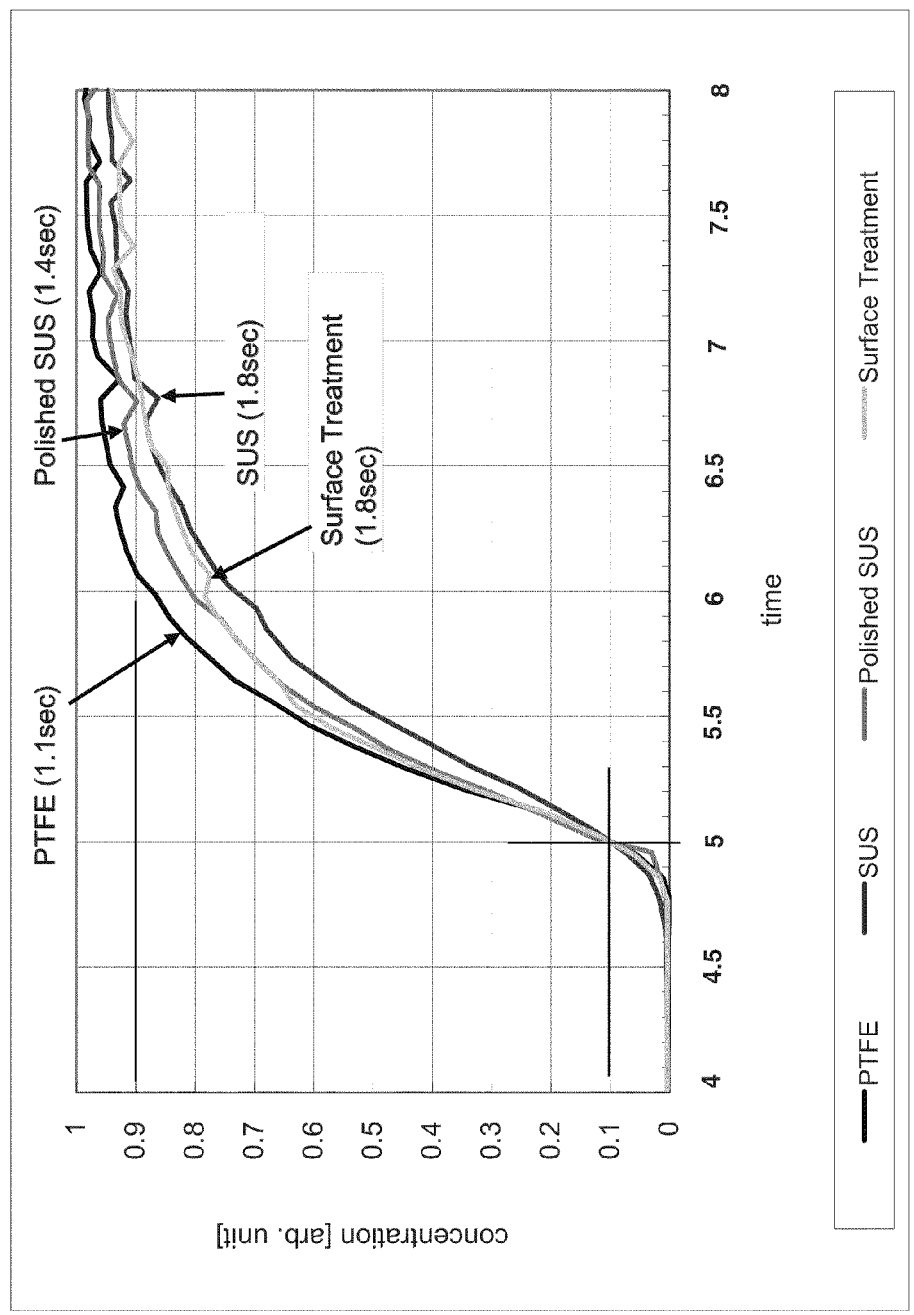
FIG. 3 is an experiment result showing a response time in case of using various kinds of heating pipes.

In case of using (1) the fluorocarbon resin (PTEE), (2) the ordinal stainless steel (SUS), (3) the mirror finished stainless steel (SUS), (4) the surface treated stainless steel (SUS) as the material of the pipe of the heating pipe 4, experiment results of the response time are shown in FIG. 3. FIG. 3 is a result measured under a condition with 50 ppm of the $NH_3$ gas, 10 L/min of the sample flow rate, 2 m of the sample piping length, a temperature of the piping at a mom temperature (about 25° C.). The response time is a period from $T_{10}$ (at a time when the measurement shows 10% concentration) to $T_{90}$ (at a time when the measurement shows 90% concentration). As is clear from FIG. 3, each of the response time is 1.1 second for the PTFE pipe, 1.8 second for the ordinal SUS pipe, 1.4 second for the mirror finished SUS pipe, 1.8 second for the surface treated SUS pipe. From these results, it becomes clear that the PTFE pipe is the most superior from a viewpoint of the response time.

In the exhaust gas analyzer 100 of this embodiment, the negative pressure pump 24 that is connected to the measurement cell 21 keeps inside of the measurement cell 21 at the negative pressure and keeps a flow channel from a downstream side of the flow rate limit part 32 (concretely, the critical flow orifice CFO2) to the measurement cell 21 at the negative pressure from a starting time of the sampling to an ending time of the measurement. Namely, the flow channel from the measurement cell 21 to the flow control limit part 32 of the heating pipe 4 becomes at the negative pressure that is generally the same pressure (for example, 25 kPa) as that of the measurement cell 21. In this embodiment, the flow channel from the downstream side of the flow rate limit part 32 (concretely, the critical flow orifice CFO2) to the measurement cell 21 comprises a flow channel in the heating pipe 4, a flow channel in the introduction port 2P and a flow channel in an internal connecting pipe 25 connecting the introduction port 2P and the measurement cell 21.

A zero gas pipe 6 to supply the measurement cell 21 with a zero gas in order to conduct zero point adjustment of the exhaust gas analyzer 100 (concretely, the light detecting part 23) and a span gas pipe 7 to supply the measurement cell 21 with a span gas in order to conduct span adjustment of the exhaust gas analyzer 100 (concretely, the light detecting part 23) are connected to the measurement cell 21. An open and close valve 61, 71 such as a solenoid valve to switch the gas supply is arranged for the zero gas pipe 6 and the span gas pipe 7 respectively. In addition, the zero gas pipe 6 and the span gas pipe 7 converges in the upstream side of the critical flow orifice (CFO) 8 as being the flow rate limit element, and the zero gas and the span gas are supplied to the measurement cell 21 through the critical flow orifice 8. The critical flow orifice 8 and the pipe near the critical flow orifice 8 are heated at, for example, 113° C. or 191° C. similar to the flow rate limit part 32 of the flow rate control unit 3. With this arrangement, it becomes possible to conduct the zero adjustment and the span adjustment under the same condition as that of the measurement.

In addition, a buffer tank 26 is arranged between the negative pressure pump 24 and the measurement cell 21. The buffer tank 26 prevents fluctuation of the flow rate of the sample gas introduced into the measurement cell 21 due to pulsation of the negative pressure pump 24. A drain separator 27 and a drain pot 28 are connected in the downstream side of the negative pressure pump 24. The exhaust gas separated from the drain by the drain separator 27 is discharged outside from the drain separator 27. In addition, the drain separated from the exhaust gas by the drain separator 27 is housed in the drain pot 28 and then discharged.

Furthermore, the flow rate limit part 32 of the flow rate control unit 3 is the critical flow orifice, and it is not possible to adjust the pressure of the sample gas introduced into the measurement cell 21 by the negative pressure pump 24 alone. Then, in this embodiment, a flow rate pressure adjust mechanism 5 to adjust the pressure of the sample gas introduced into the measurement cell 21 is arranged. The flow rate pressure adjust mechanism 5 is arranged on the connecting pipe between the negative pressure pump 24 and the measurement cell 21 and comprises a flow channel 51 to introduce a compensation gas such as atmospheric air, a filter 52 arranged on the flow channel 51 and a regulator 53 such as a pressure adjusting valve to adjust a flow rate of the compensation gas. The regulator 53 adjusts the pressure of the compensation gas so as to make inside of the measurement cell 21 at a constant pressure. Since a regulator is not arranged between the exhaust pipe and the measurement cell 21, there is in no danger of $NH_3$ adsorption by the regulator. In this embodiment, the flow channel 51 is connected to the buffer tank 26.

Effect of this Embodiment

In accordance with the exhaust gas analyzer 100 of this embodiment having the above-mentioned arrangement, since the flow rate limit part 32 is arranged in the upstream side end part of the heating pipe 4 arranged outside of the body 2 and inside of the measurement cell 21 and the flow channel from the downstream side of the flow rate limit part 32 to the measurement cell 21 are made at the negative pressure, it is possible to enlarge the area at the negative pressure of the flow channel connecting to the measurement cell 21 as much as possible, thereby enabling to reduce adsorption of the $NH_3$ component. In addition, since the flow rate limit part 32 is arranged and the negative pressure is kept by the negative pressure pump 24 from the starting time of the sampling to the ending time of the measurement, it is possible to prevent the downstream side of the flow rate limit part 32 from being at a positive pressure due to a flowing pressure of the sample gas, thereby enabling to prevent attachment of the $NH_3$ component. With this arrangement, it is possible to conduct the measurement with high accuracy even though the concentration of the $NH_3$ component is low, and furthermore it is possible to improve the response speed of measuring the concentration. Since the $NH_3$ component is difficult to be detached if once adsorbed, it is required to keep the negative pressure on a constant basis from the starting time of the sampling to the ending time of the measurement.

In addition, since the flow rate limit part 32 is arranged in the upstream side end part of the heating pipe 4, the negative pressurized sample gas is heated, thereby enabling further to prevent a dissolution loss of the $NH_3$ component associated with due condensation in the heating pipe 4.

Furthermore, if the absorption spectrum at an atmospheric pressure is monitored, it is known that the absorption peak is wide. Then, if inside of the measurement cell 21 is kept at the negative pressure, it is possible to obtain a sharper peak, thereby enabling to reduce an interference influence on the absorption peak of the $NH_3$ component.

Other Modified Embodiment

The present claimed invention is not limited to the above-mentioned embodiment.

For example, in the above-mentioned embodiment, the flow rate limit part is arranged in the upstream side end part of the heating pipe 4 so as to maximize the negative pressurized flow rate volume, however, the flow rate limit part may be arranged on the heating pipe.

In addition, in addition to the critical flow orifice, a vacuum regulator such as a pressure adjust valve, a capillary, or a venturi may be used as the flow rate limit part.

Furthermore, in the above-mentioned embodiment, the $NH_3$ component is explained as the adsorptive gas, however, a gas component of high adsorption such as a hydrocarbon (HC) component may be analyzed. As an example of the hydrocarbon (HC) component represented are aromatic hydrocarbon such toluene, alcohol such as methanol or ethanol, and high boiling point hydrocarbon (HC). In addition, as the high adsorptive gas component represented is a molecule having a polar character such as $NO_2$, $SO_2$, and $H_2O$.

In the above-mentioned embodiment, the body 2 and the flow rate control unit 3 are separately arranged, however, they may be integrally formed.

In addition, the present claimed invention is not limited to the above-mentioned embodiment and it is a matter of course that various modification can be made without departing from a spirit of the invention.

EXPLANATION OF CODE

100 . . . exhaust gas analyzer (adsorptive gas analyzer)
2 . . . body
21 . . . measurement cell
2P . . . introduction port
22 . . . laser light irradiation part
24 . . . negative pressure pump
32 . . . flow rate limit part
4 . . . heating pipe

The invention claimed is:
1. An adsorptive gas analyzer to measure a concentration of an adsorptive component having a polar character contained in a sample gas, the adsorptive gas analyzer comprising:

a body that has a measurement cell to measure the sample gas and an introduction port to introduce the sample gas into the measurement cell;

a laser light irradiation part that irradiates laser light on the measurement cell;

a heating pipe that applies heat to the sample gas introduced into the introduction port, that has an inlet end, and that has an outlet end connected to the introduction port of the body;

a flow rate control unit arranged separately from the body and including a flow rate limit part that makes the sample gas at a negative pressure, that introduces the heated negative-pressurized sample gas into the body via the heating pipe, and that is connected to the inlet end of the heating pipe; and a negative pressure pump that is connected to the measurement cell, that keeps inside of the measurement cell at the negative pressure from a starting time of a sampling to an ending time of the measurement, and that keeps a flow channel from a downstream side of the flow rate limit part to the measurement cell at the negative pressure from the starting time of the sampling to the ending time of the measurement.

2. The adsorptive gas analyzer described in claim 1, wherein the measurement cell is of a multiple reflection type.

* * * * *